United States Patent
Rothschild et al.

(10) Patent No.: US 6,356,620 B1
(45) Date of Patent: Mar. 12, 2002

(54) METHOD FOR RASTER SCANNING AN X-RAY TUBE FOCAL SPOT

(75) Inventors: Peter Rothschild, Newton; Lee Grodzins, Lexington, both of MA (US)

(73) Assignee: American Science & Engineering, Inc., Billerica, MA (US)

( * ) Notice: Subject to any disclaimer, the term of this patent is extended or adjusted under 35 U.S.C. 154(b) by 0 days.

(21) Appl. No.: 09/625,686

(22) Filed: Jul. 26, 2000

Related U.S. Application Data

(60) Provisional application No. 60/146,465, filed on Jul. 30, 1999, and provisional application No. 60/154,524, filed on Sep. 16, 1999.

(51) Int. Cl.[7] .................................................. G21K 5/10
(52) U.S. Cl. ........................ 378/146; 378/137; 378/160
(58) Field of Search ................................. 378/119, 121, 378/137, 143, 146, 147, 160

(56) References Cited

U.S. PATENT DOCUMENTS

| | | | | |
|---|---|---|---|---|
| 5,267,294 A | * | 11/1993 | Kuroda et al. | 378/65 |
| 5,493,596 A | * | 2/1996 | Annis | 378/57 |
| 6,009,146 A | * | 12/1999 | Adler et al. | 378/98.6 |

\* cited by examiner

*Primary Examiner*—Robert H. Kim
*Assistant Examiner*—Jurie Yun
(74) *Attorney, Agent, or Firm*—Bromberg & Sunstein LLP

(57) ABSTRACT

A method and apparatus for producing a scanned beam of penetrating radiation. A beam of particles illuminates a portion of a target, the illuminated portion comprising a focal spot having a centroid. Illumination of the target creates a beam of penetrating radiation such as x-rays. The beam of particles is swept across the target in such a manner that the centroid of the focal spot lies on a line defined by the instantaneous direction of the beam of penetrating radiation as defined, in turn, by a collimating path.

14 Claims, 4 Drawing Sheets

METHOD FOR RASTER SCANNING AN X-RAY TUBE FOCAL SPOT

The present application claims priority from U.S. Provisional Applications, Serial Nos. 60/146,465, filed Jul. 30, 1999, and 60/154,524, filed Sept. 16, 1999, both of which applications are incorporated herein by reference.

TECHNICAL FIELD

The present invention relates to a method for providing a source of penetrating radiation for a scanning imaging system having a varying collimation path, wherein the target of an x-ray tube is scanned in such a manner as to reduce the focal spot size while maintaining stability of the origin of the penetrating radiation with respect to the collimation path.

BACKGROUND OF THE INVENTION

Various x-ray systems, such as those used for backscatter imaging of articles or containers, employ a rotating collimator wheel to create a scanning beam of x-rays, such as shown, for example, in U.S. Pat. No. 5,764,683, which is herein incorporated by reference. One method for generating a scanning beam of x-rays is shown in FIG. 1. An x-ray tube 60 is in the center of a mechanical scanner 66 which includes a rotating wheel 61 of material substantially opaque to x-rays except in the paths defined by hollow spokes 62. X-ray tube 60 generates x-rays by bombarding a target with a beam of particles, typically electrons, emerging from a direction having a component transverse to the plane of the drawing. X-ray beams 64 sweep in the plane of the drawing over an object 68, which may be a container in which articles are concealed, for example. Scattered x-rays 72 are detected by scatter detector 74. An image of the intensity of x-rays scattered by object 68, or transmitted through object 68, may be obtained as object 68 is conveyed through the scanned x-rays by a conveyor 70. Alternatively, object 68 may be fixed while x-ray beams 64 and/or detector 74 are swept.

Mechanical scanner 66 is typically a massive and ponderous component since rotating wheel 61 must be opaque to the penetrating radiation being scanned and is thus typically made out of lead of sufficient thickness to stop the most energetic x-rays produced by x-ray tube 60. It is thus advantageous that the collimator wheel be small. Reduction of the size of the collimator wheel may be limited by the size of the region of the x-ray tube target onto which the electron beam is focused. The size of the emission region may be limited in turn, for a specified output flux, to a minimal size governed by the power dissipation capacity of the x-ray tube target.

For x-ray imaging systems that use a beam of x-rays, the size of the focal spot on the x-ray tube target is a limiting factor for the resolution of the image that is obtained. A smaller focal spot results in a higher image resolution. The size of the focal spot is limited, however, by the amount of power that can be dissipated in the target by the incident electron beam. If the focal spot is large, the electron energy is dissipated over a relatively large area of the target, without overheating any one area of the target. If the focal spot is too small, the energy density in the focal spot is very high which can lead to overheating and melting of the target in a relatively short time. A small focal spot can be safely used, however, if the focal spot is not stationary on the target, but is raster-scanned across the target. This prevents the focal spot from being incident on any one area of the target for a period exceeding the dissipation capacity of the material of the target and allows the focal spot to be moved to another area of the target before any damage occurs.

SUMMARY OF THE INVENTION

In accordance with a preferred embodiment of the present invention, there is provided a method for producing a scanned beam of penetrating radiation. The method has the steps of:

a. illuminating a portion of a target with a beam of particles, the target having an effective center, the portion of the target illuminated by the beam of particles comprising a focal spot having a centroid, the illumination being such as to create a beam of penetrating radiation;

b. directing the beam of penetrating radiation through a collimating path having an instantaneous direction defining a line; and c. scanning the beam of particles across the target in such a manner that the centroid of the focal spot lies on the line defined by the instantaneous direction of the collimating path.

In accordance with other embodiments of the present invention, the beam of penetrating radiation may be a pencil beam, the penetrating radiation may include x-rays, and the beam of particles may be an electron beam. The step of directing the beam of penetrating radiation may include steering the particle beam across the target by electromagnetic means.

In accordance with yet other embodiments of the invention, there is provided an apparatus for scanning a beam of penetrating radiation across an object. The apparatus has a source of penetrating photons having a beam of particles incident upon a target at a region of incidence such that penetrating photons are emitted from the region of incidence into a penetrating beam. Additionally, the apparatus has a collimator that allows propagation of a beam of penetrating photons along an instantaneous direction defining a line as well as a particle beam steering arrangement for selecting the region of incidence of the beam of particles upon the target in such a manner that the centroid of the region of incidence of the beam of particles lies on the line defined by the instantaneous direction of the penetrating photons. The apparatus may also have a penetrating beam director for defining the instantaneous direction of the penetrating photons. The penetrating beam director may be a chopper wheel, or a slit rotating with respect to a fixed axis, or a pair of slits, the slits counterrotating with respect to a fixed axis.

BRIEF DESCRIPTION OF THE DRAWINGS

The foregoing features of the invention will be more readily understood by reference to the following detailed description taken with the accompanying drawings in which.

DETAILED DESCRIPTION OF PREFERRED EMBODIMENTS

In accordance with preferred embodiments of the present invention, electromagnetic fields may be used to raster scan the focal spot of an x-ray tube across the x-ray tube target, thereby advantageously allowing a smaller focal spot to be obtained without requiring additional power dissipation capacity.

Figure 1:
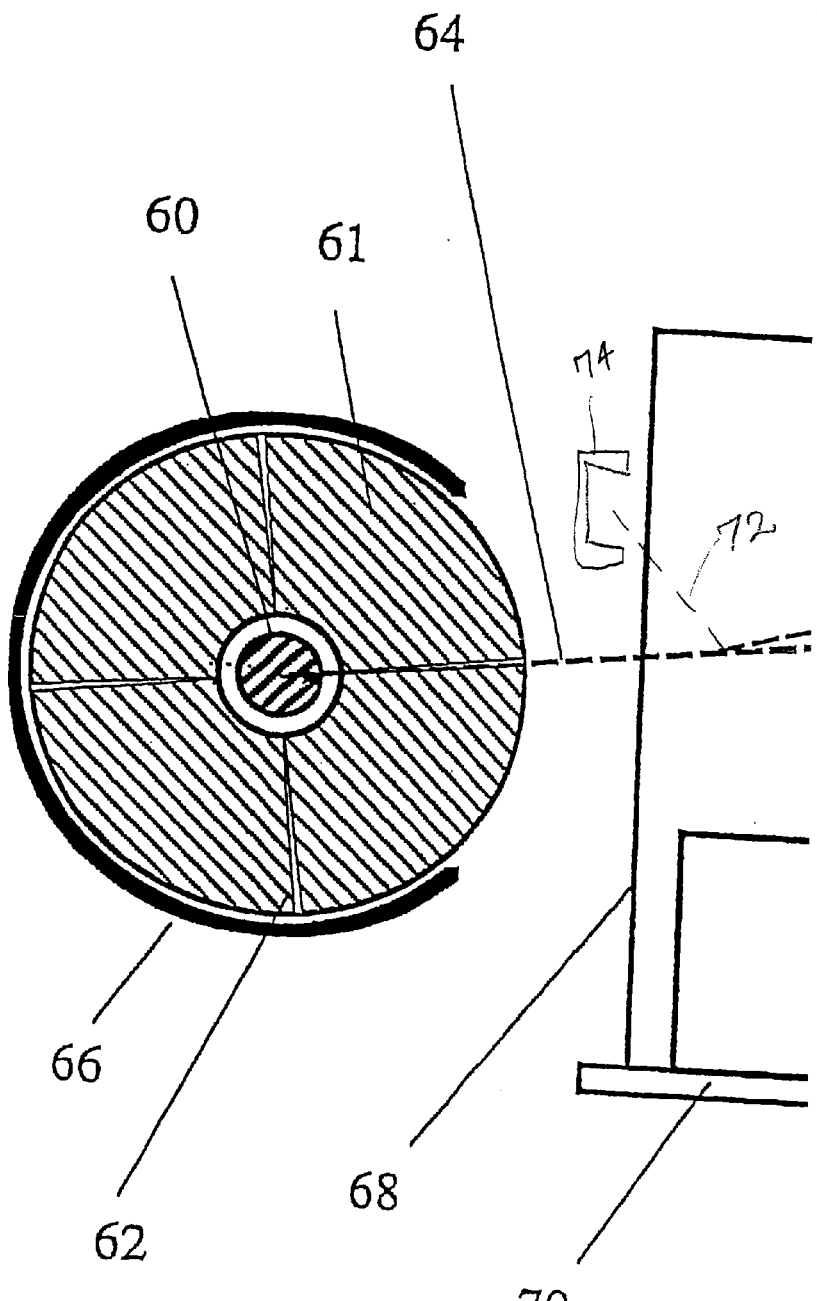
FIG. 1 shows a diagram of a prior art x-ray inspection system including a mechanical scanner for sweeping an x-ray beam across an object.
Figure 2:
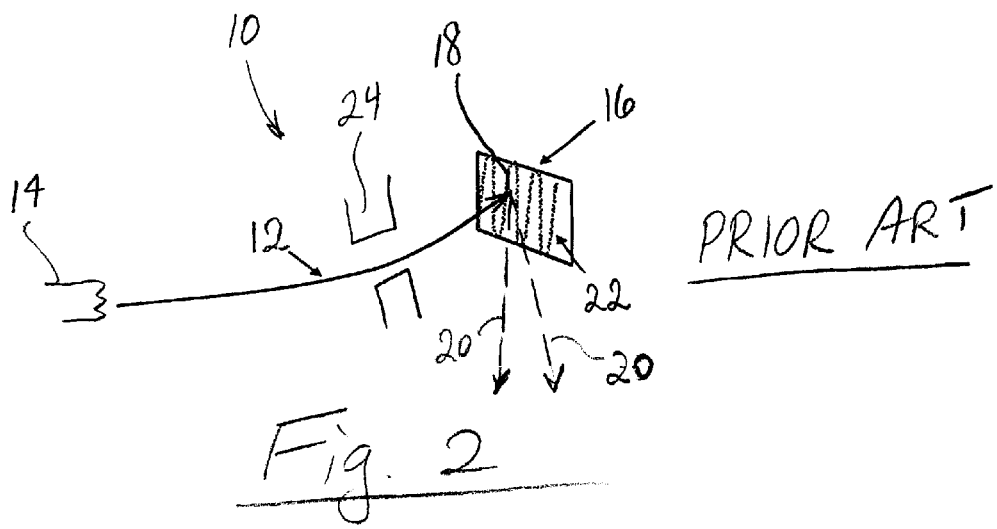
FIG. 2 shows the scanning of a charged particle beam across a target for generating x-rays, as employed in the present invention.

Fundamental components of a typical x-ray generator 10 are described with reference to FIG. 2. A beam 12 of charged particles is emitted by a particle source 14 which, in the case of electrons, is typically a cathode. Beam 12 of charged particles may be referred to herein, without limitation, as an electron beam, though reversal of electrical polarities, in the case of a beam of positive ions, is known to persons skilled in the art and is within the scope of the present invention. Electron beam 12 is accelerated toward target 16 either by virtue of a positive electrical potential applied to target 16 with respect to cathode 14 or by means of one or more accelerating grids intervening between cathode 14 and target 16 as known to persons skilled in the electronic arts. The size of focal spot 18, where electron beam 12 impinges upon target 16, defines the region of target 16 that emits x-ray emission 20, and may thus be a limiting factor in the resolution of any image obtained using x-ray emission 20.

As discussed in the background section above, the size of focal spot 18 also determines the electron energy density that must be dissipated by target 16. If focal spot 18 is scanned across target 16, such as along the two-dimensional pattern designated generally by the dotted line denoted 22, the electron energy may be dissipated over a larger area of target 16 than if the focal spot remains stationary. Steering of beam 12 may be provided by any of a variety of electromagnetic steering arrangements such as, by way of example, magnetic coils 24 placed around the trajectory of beam 12 or by means of an electrostatic lens. Additionally, as known to persons skilled in the art of x-ray tubes, the size and shape of beam 12 as it impinges upon target 16 may also be adjusted by operation of steering arrangement 24. The focal spot can be raster-scanned across target 16 in two dimensions much like the electron beam in a television cathode ray tube, or it can be raster-scanned in only one dimension. Clearly, the size of the focal spot can be made smaller with a two dimensional scan because the electron beam energy is dissipated over a larger area of the target. The raster scanning can be achieved, for example, by applying a sinusoidal waveform to coils 24. Other waveforms can be used depending on the scanning pattern that is advantageous in a particular application.

Figure 3:
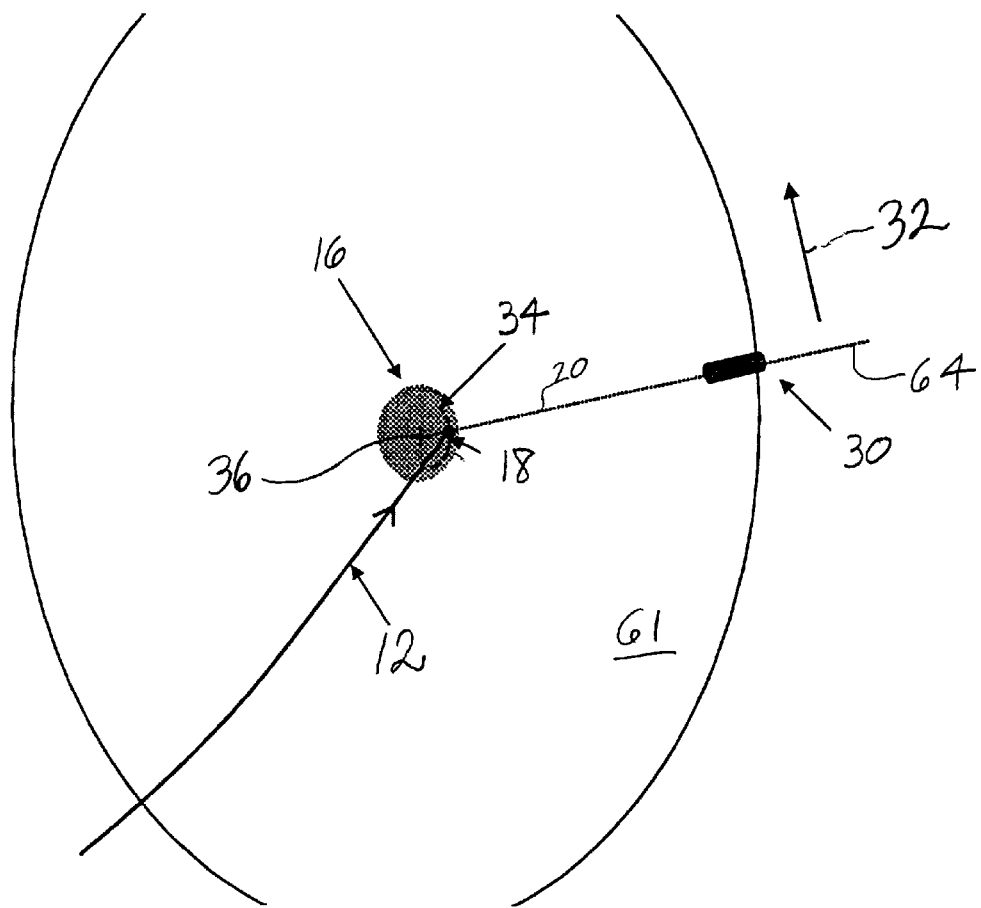
FIG. 3 shows the relative orientation of the instantaneous collimation path and the scanned x-ray tube focal spot in accordance with an embodiment of the present invention.

Referring now to FIG. 3, application of the scanning of the focal spot 18 of electron beam 12 across the face of target 16 is now discussed in the context of a system in which the direction of x-ray beam 64 is varied for purposes of imaging in accordance with preferred embodiments of the invention. In the embodiment depicted in FIG. 3, x-ray beam 64 has a substantially circular cross section and is a "pencil" beam. Direction 64 (also representing the x-ray beam) is an instantaneous direction of propagation, as defined by collimator jaw 30. The position of collimator jaw 30 relative to the source of x-ray beam 20 is typically varied as a function of time by a beam director which may be a mechanical chopper wheel 61 or, alternatively, may be an oscillating slot mechanism or other beam direction arrangement, some of which mechanisms are discussed below in the context of alternate embodiments of the invention.

X-rays 20 are blocked from propagating along any direction other than through collimator jaw 30 by virtue of the x-ray opacity of the beam director 61, shown here as a rotating chopper wheel. As chopper wheel 61 rotates in a counterclockwise direction, x-ray beam 64 is sweep in the direction designated by arrow 32. The center of rotation of chopper wheel 61 defines an effective center 36 on the surface of target 16.

In accordance with preferred embodiments of the invention, focal spot 18 is scanned along a scan path 34 such that the centroid of focal spot 18 always lies instantaneously on line 64 along which x-rays are emitted by the collimator. In the case of rotation of chopper wheel 61 about effective center 36, the centroid of focal spot 18 lies, more particularly, along the line defined by effective center 36 and the central bore of collimator jaw 30. Thus, the centroid of focal spot 18 is scanned in an arc in synchrony with the change in direction of the beam 64 of penetrating radiation. As a result of the operation as described, the distribution of emitted x-rays 20 is always similarly located with respect to collimator jaw 30 and distortion of the beam as viewed along beam direction 64 will thereby be advantageously minimized.

The size of the collimator wheel is determined by the required image resolution and the size of the x-ray tube focal spot. By reducing the focal spot size, the collimator wheel may be made smaller (without degrading the image resolution). By raster scanning the focal spot in one dimension across the target, as described above, the size of the focal spot can be reduced, while maintaining a constant average energy density on the target. Thus, a reduction in the size of the collimator wheel is facilitated. By aligning the direction of the one-dimensional raster scan with the direction of the x-ray beam sweep, adverse affects on the image quality due to the raster scanning of the focal spot are advantageously reduced.

Figure 4:
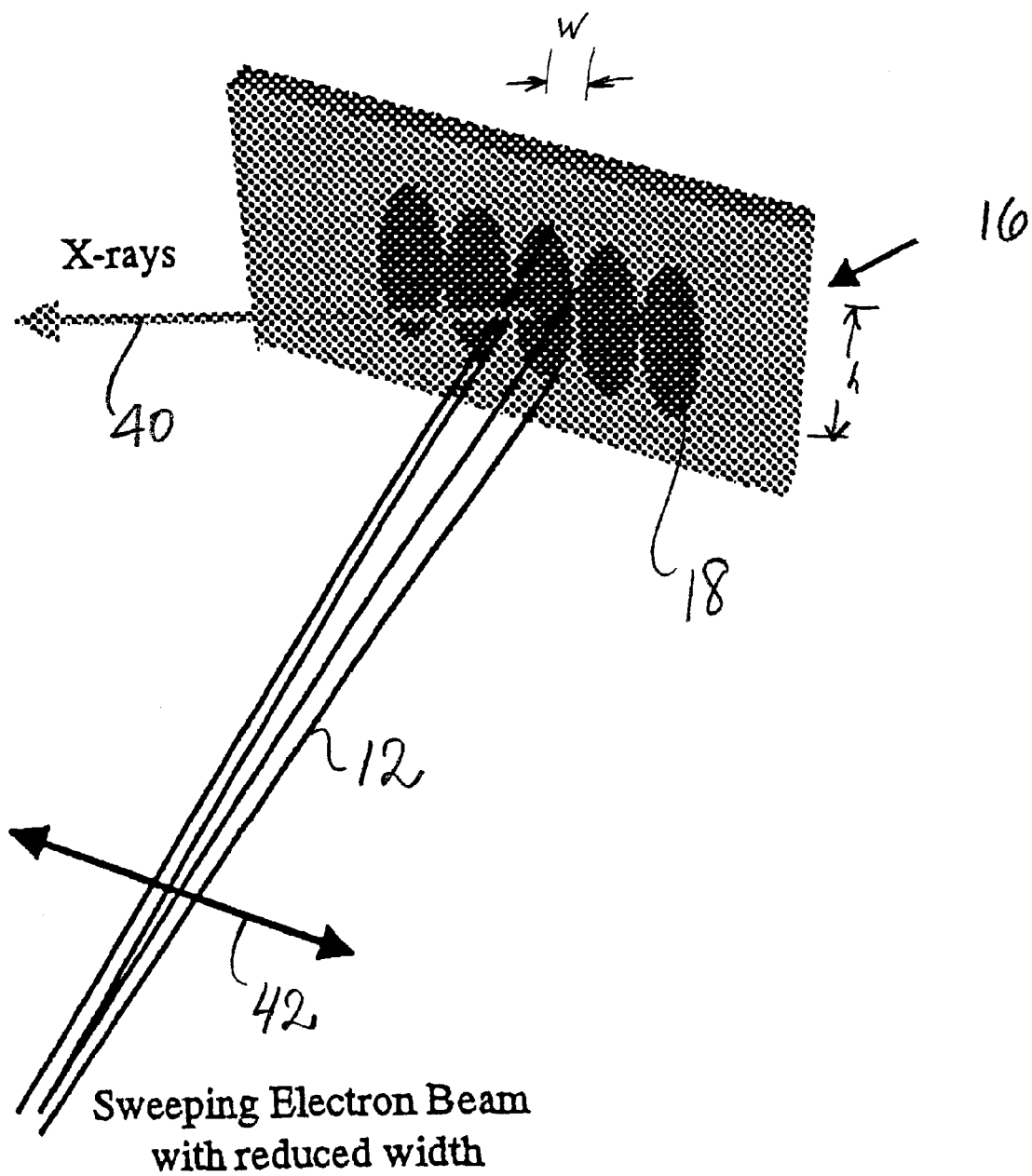
FIG. 4 shows the scanning of a charged particle beam having a reduced width in the direction of scanning across a target for generating x-rays in accordance with an embodiment of the present invention.

In accordance with embodiments of the present invention, the dimensions of the focal spot 18 incident on target 16 may be asymmetrical with respect to its dimensions in the directions parallel and perpendicular to the direction of scanning of the beam. Thus, as shown in FIG. 4, width w of focal spot 18 in direction 40 corresponding to the direction of extraction of x-rays from target 16 is smaller, typically by a factor of approximately 5, from that typically employed for a fixed focal spot. The height h of focal spot 18 is comparable to that employed for a fixed focal spot arrangement. Electron beam 12 is swept across target 16 in direction 42, such as by applying a periodic input voltage, such as a sinusoidal voltage, for example, to deflection coils 24 (shown in FIG. 2). Thus, while the focal spot is smaller, the time averaged power per unit area on the target is advantageously reduced and local overheating of the target may be prevented.

By applying the teachings provided in the above discussion, a uranium wheel of a diameter smaller by a factor of four from a diameter typical for a particular application may be employed.

It is to be understood that embodiments other than rotation of the spokes of a chopping wheel may be used in accordance with the invention for creating a scanning beam of x-rays. Thus, for example, a slit may be translated relative to the source of penetrating radiation in order to form a scanning fan beam. In this case, in accordance with an alternate embodiment of the invention, a focal region of incidence of the particle beam on the target, having a substantially rectangular shape, may be scanned across the target subject to a constraint analogous to that described above: namely, the focal region lies in a plane instantaneously containing the emitted fan beam, possibly relative to an effective vertex of motion of the scanning beam.

In accordance with an alternate embodiment of the concept heretofore described, a translated linear slit 48 is described with reference to FIG. 5. An electron beam (designated by numeral 12 in FIG. 2) is incident, from a direction directed substantially out from behind the plane of the page, onto an arcuate target or anode 16. A tungsten cylinder 50 rotates about an axis 52 perpendicular to the plane of the page thereby scanning slit 48 in synchrony with the motion of focal spot 18 on the face of anode 16. Axis 52 coincides with the center of curvature of anode 16 such that the emitted x-ray beam always passes through the center of curvature 52. Shielding 54, typically lead, is provided so that x-ray radiation is emitted only via slit 48. Cylinder 50 has a transverse collimating hole 56 defining the size of the emitted beam of penetrating radiation. With a single slit 48 as shown, an x-ray beam is emitted approximately 40% of the time. If two perpendicular slits are used, the beams exit 80% of the time. The 20% dead time may be used for flyback of the electron beam to begin the scanning cycle of focal spot 18 on target 16.

Figure 5:
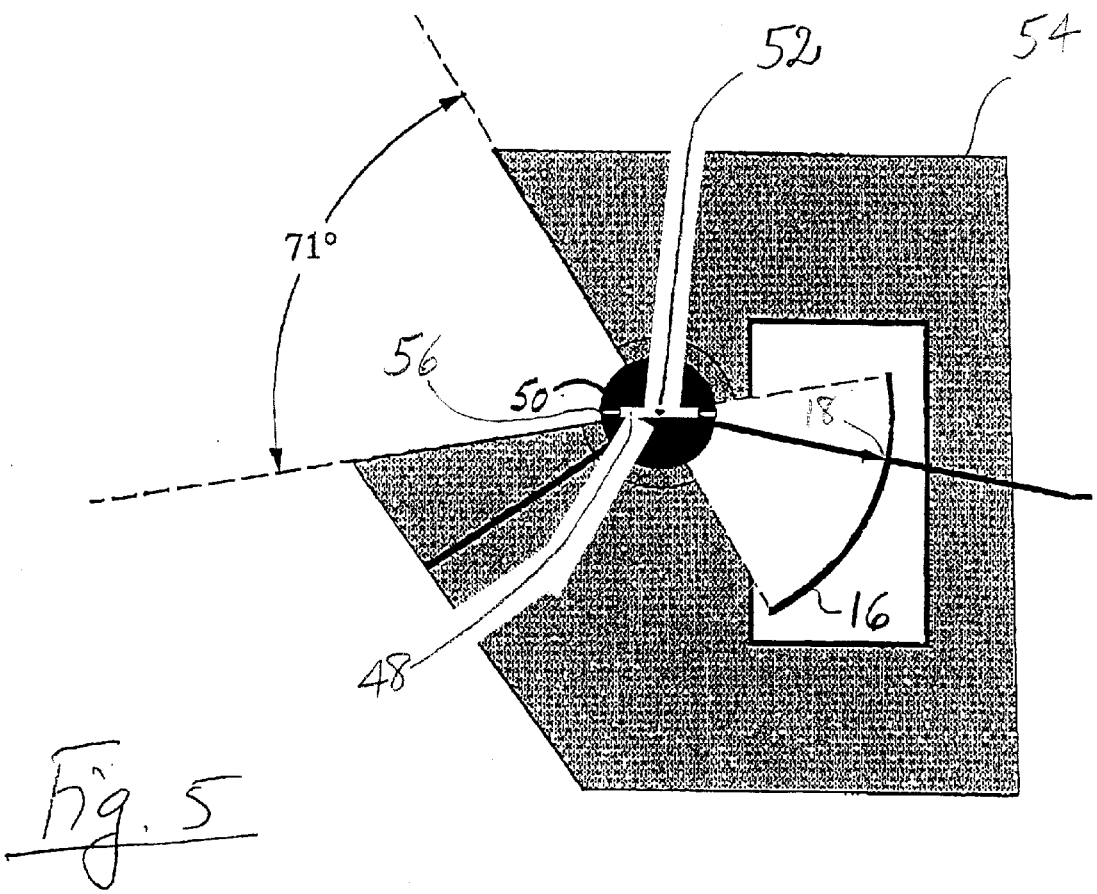
FIG. 5 shows a scanning slit for collimating an x-ray beam generated by scanning the focal spot of a charged particle across a target in accordance with an embodiment of the present invention.

Advantages of the rotating slip embodiment of FIG. 5 include the smaller size of the rotating element and the flexibility afforded in the placement of the x-ray anode and its shielding and cooling. Additionally, the x-ray beam may advantageously be taken off in the forward direction with respect to the electron beam, with an attendant gain in the power and energy of the x-ray spectrum, especially at high electron energies. Additionally, the linear scan length (in the dimension into the page) may be extended relative to the limited axial opening of a chopper wheel configuration.

Figure 6:
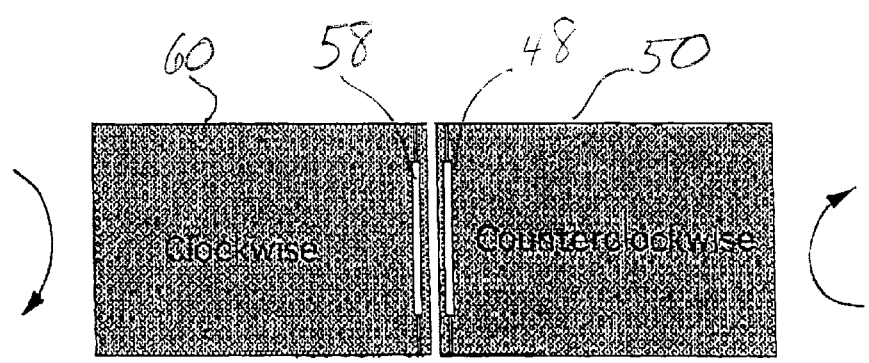
FIG. 6 shows, in cross section, a pair of counterrotating slits for generating a high duty cycle scanning x-ray beam in accordance with an embodiment of the present invention.

Referring now to FIG. 6, a pair of counter-rotating slits 48 and 58 are shown in cross-section, for generating a high duty cycle scanning x-ray beam in accordance with an alternate embodiment of the present invention. A first cylinder 50 rotates in a clockwise sense, in synchrony with the scanning of a focal spot of the electron beam onto a target during a portion of a cycle, whereas a second cylinder 60 counter-rotates with respect to first cylinder 50, but is in synchrony with the scanning focal spot of the electron beam onto the target during a second portion of the cycle. The electron beam oscillates along two closely parallel arcs on the anode, thus, the electron beam moves up along a first arc, generating s-rays that pass through first cylinder 50, then jogs and moves down a second arc, generating s-rays that pass through the collimator of the abutting second cylinder 60.

In accordance with a further embodiment of the invention, the integrity of the x-ray beam exiting from the collimator may be enhanced by providing a signal based on the angular position of the collimating cylinder to control the steering coil that governs the direction of the electron beam in the x-ray generator.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for producing a scanned beam of penetrating radiation, the method comprising:
 a. illuminating a portion of a target with a beam of particles, the target having an effective center, the portion of the target illuminated by the beam of particles comprising a focal spot having a centroid, the illumination being such as to create a beam of penetrating radiation;
 b. directing the beam of penetrating radiation through a collimating path having an instantaneous direction defining a line; and
 c. scanning the beam of particles across the target in such a manner that the centroid of the focal spot lies on the line defined by the instantaneous direction of the collimating path.

2. A method in accordance with claim 1, wherein the beam of penetrating radiation is an x-ray beam.

3. A method in accordance with claim 1, wherein the beam of penetrating radiation is a pencil beam.

4. A method in accordance with claim 1, wherein the beam of particles is an electron beam.

5. A method in accordance with claim 1, wherein the step of directing the beam of penetrating radiation includes steering the particle beam across the target by electromagnetic means.

6. A method in accordance with claim 1, wherein the instantaneous direction of the beam of penetrating radiation changes along an arcuate path.

7. A method in accordance with claim 6, wherein the centroid of the focal spot is scanned along the arcuate path in synchrony with the instantaneous direction of the beam of penetrating radiation.

8. A method in accordance with claim 6, wherein the instantaneous direction of the beam of penetrating radiation oscillates with respect to a central direction.

9. An apparatus for scanning a beam of penetrating radiation across an object, the apparatus comprising:
 a. a source of penetrating photons having a beam of particles incident upon a target at a region of incidence of the beam of particles upon the target, the region of incidence having a centroid, such that penetrating photons are emitted from a region of incidence of the beam of particles upon the target into a penetrating beam;
 b. a collimator that allows propagation of penetrating photons along an instantaneous direction defining a line; and
 c. a particle beam steering arrangement for selecting the region of incidence of the beam of particles upon the target in such a manner that the centroid of the region of incidence of the beam of particles lies on the line defined by the instantaneous direction of the penetrating photons.

10. An apparatus according to claim 9, wherein the source of penetrating photons is an x-ray tube.

11. An apparatus according to claim 9, further including a penetrating beam director for providing a varying direction of illumination by the penetrating beam.

12. An apparatus according to claim 11, wherein the penetrating beam director includes a chopper wheel.

13. An apparatus according to claim 11, wherein the penetrating beam director includes a slit rotating with respect to a fixed axis.

14. An apparatus according to claim 11, wherein the penetrating beam director includes a pair of slits, the slits counterrotating with respect to a fixed axis.

* * * * *